US00PP10230P

United States Patent [19]

Zary

[11] Patent Number: Plant 10,230

[45] Date of Patent: Feb. 10, 1998

[54] HYBRID TEA ROSE PLANT NAMED 'JACIRST'

[75] Inventor: Keith W. Zary, Thousand Oaks, Calif.

[73] Assignee: Bear Creek Gardens, Inc., Medford, Oreg.

[21] Appl. No.: 759,988

[22] Filed: Dec. 3, 1996

[51] Int. Cl.[6] ..... A01H 5/00

[52] U.S. Cl. ..... Plt./17

[58] Field of Search ..... Plt./20, 19, 17, Plt./16

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the hybrid tea class, having large, coral-orange flowers; long stems; a vigorous, upright growth habit; and large, dark green, leathery foliage.

1 Drawing Sheet

The present invention relates to a new and distinct variety of rose plant of the hybrid tea class which was originated by me by crossing the variety JACbor, U.S. Plant Pat. No. 6,668, with the variety JACyo, U.S. Plant Pat. No. 6,443.

The primary objective of this breeding was to produce a new rose variety having the large flowers and healthy, dark green foliage of the female parent combined with the very vigorous, upright growth habit and long flowering stems of the male parent. Expected flower color was intermediate between the two parents. The objective was substantially achieved, along with other desirable improvements, as evidenced by the following unique combination of characteristics that are outstanding in the new variety and that distinguish it from its parents, as well as from all other varieties of which I am aware:

1. Large coral-orange flowers;
2. Vigorous, upright habit of growth;
3. Large, dark green, leathery foliage; and
4. Long stems.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACbor, U.S. Plant Pat. No. 6,668.

*Pollen parent.*—JACyo, U.S. Plant Pat. No. 6,443.

Classification:

*Botanical.*—*Rosa hybrida.*

*Commercial.*—Hybrid tea.

FLOWER

Observations made from specimens grown from March through September, 1996 in a garden environment at Somis, Calif.

Blooming habit: Recurrent.

Bud:

*Size.*—1¾ to 2 inches long when the petals start to unfurl.

*Form.*—The bud form is long, pointed ovoid.

*Color.*—When sepals first divide, bud color is Red Group 43A. When half blown, the upper sides of the petals are Red Group 43C; and the lower sides of the petals are Red Group 43D.

*Sepals.*—Color: Green Group 138B. Surface texture: Covered in fine hairs. There are three lightly appendaged sepals. There are two unappendaged sepals with hairy edges.

*Receptacle.*—Color: Green Group 137D. Shape: Funnel. Size: Medium (⅜ inch×⅜ Inch). Surface: Smooth.

*Peduncle.*—Length: Short (2 to 2¼ inches). Surface: Smooth. Color: Light green and bronzy. Strength: Stiff, erect.

Bloom:

*Size.*—Large. Average open size is 5 to 5½ inches.

*Borne.*—Singly.

*Stems.*—Long. Average length is about 20 to 24 inches.

*Form.*—When first open: High centered. Permanence: Outer petals curl back.

*Petalage.*—Number of petals under normal conditions: 35 to 40.

*Color.*—The upper side of the petals is Red Group 43C. The reverse side of the petals is Red Group 43D. The base of each petal has a small (3/16 inches×3/16 inches), white half moon at the point of attachment. The major color on the uper side is Red Group 43C.

*Variegations.*—None.

*Discoloration.*—The general tonality at the end of the first day: No change. At the end of the third day: There is a color change to Red Group 39B on the petals in the center of the flower as they become fully exposed to sunlight. This change spreads to the entire flower by day five. By day six, petal drop has begun.

*Fragrance.*—Moderate.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long (5 or 6 days). As a cut flower: Long (8 or 9 days).

Reproductive parts:

*Anthers.*—Size: Medium. Quantity: Many. Color: Yellow. Arrangement: Regular around styles.

*Filaments.*—Color: Reddish brown.

*Pollen.*—Color: Gold yellow.

*Styles.*—Color: Red.

*Stigmas.*—Color: Greenish white.

Form: Bush.

Growth: Very vigorous, upright, branching. Height at one year of a plant grown in Southern California without pruning will be over 6 feet, while the width will be 4 to 4½ feet.

Foliage: Number of leaflets on normal mid-stem leaves: 5.

*Size.*—Large (5½×4½ inches).

*Quantity.*—Abundant.

*Color.*—New foliage: Upper and lower surfaces are Purple Group 183A. Old foliage: Upper surface is Green Group 139A; lower surface is Green Group 139B.

Leaflets:

*Shape.*—Broadly oval.

*Texture.*—Upper side: Leathery.

*Edge.*—Serrated.

*Serration.*—Single, small.

*Petiole rachis.*—Color: Reddish.

*Petiole underside.*—Smooth, with an occasional prickle.

*Stipules.*—Short (⅜ inch); serrated.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜ inch to ¼ inch), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its large, well formed coral-orange flowers; its long stems; its vigorous, upright habit of growth; and its large, dark green, leathery foliage.

* * * * *

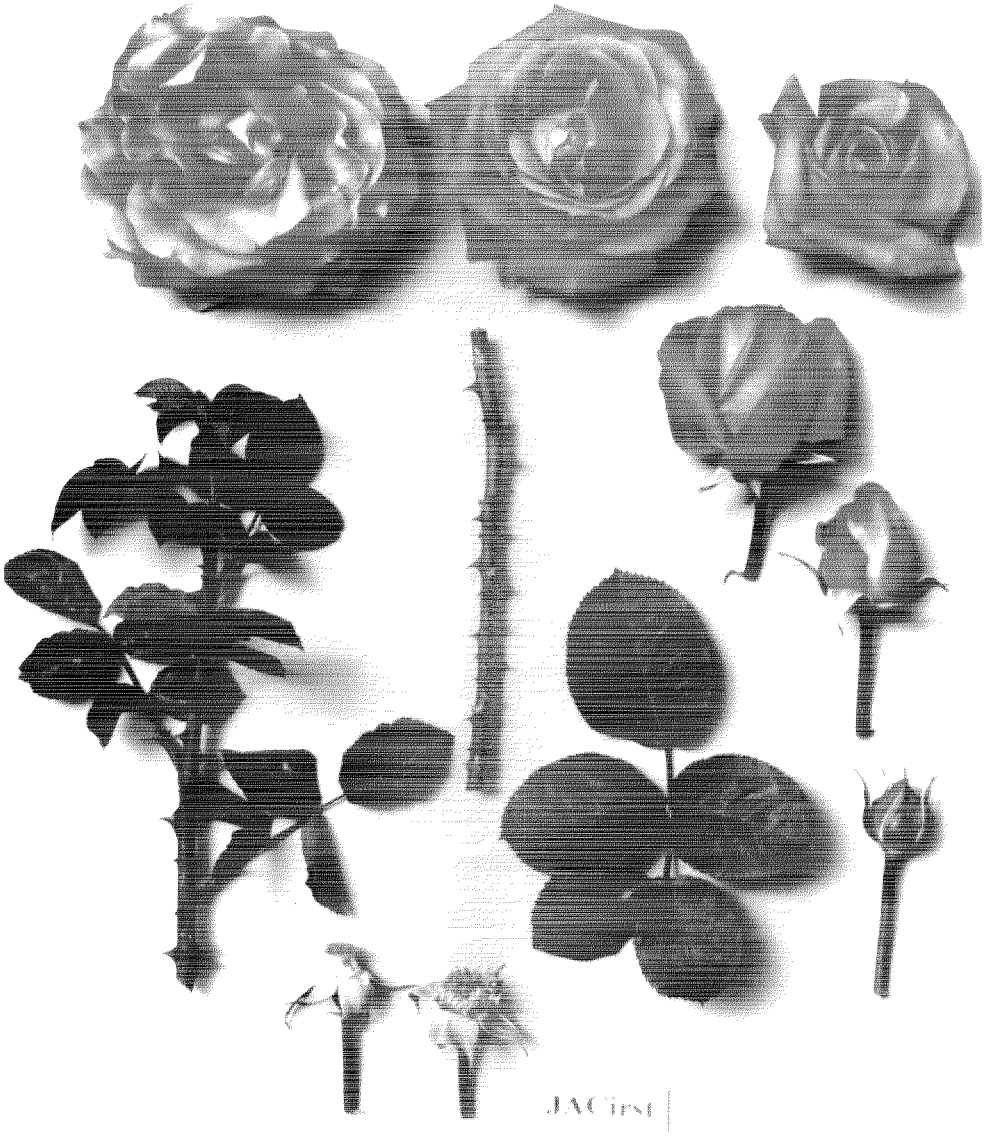
JACirsi